(12) United States Patent
Llewellyn, Jr.

(10) Patent No.: US 9,286,771 B2
(45) Date of Patent: Mar. 15, 2016

(54) SYSTEM AND METHOD FOR PROVIDING NEED SPECIFIC SERVICE IDENTIFIERS

(71) Applicant: Bruce Llewellyn, Jr., Jacksonville, FL (US)

(72) Inventor: Bruce Llewellyn, Jr., Jacksonville, FL (US)

(*) Notice: Subject to any disclaimer, the term of this patent is extended or adjusted under 35 U.S.C. 154(b) by 206 days.

(21) Appl. No.: 13/651,433

(22) Filed: Oct. 14, 2012

(65) Prior Publication Data

US 2013/0099930 A1   Apr. 25, 2013

Related U.S. Application Data

(60) Provisional application No. 61/550,911, filed on Oct. 24, 2011.

(51) Int. Cl.
| G08B 5/22 | (2006.01) |
| G07C 11/00 | (2006.01) |
| G08B 1/08 | (2006.01) |
| G08B 23/00 | (2006.01) |
| G09B 21/00 | (2006.01) |
| G08B 3/10 | (2006.01) |
| G06F 19/00 | (2011.01) |
| G06Q 50/22 | (2012.01) |
| G06Q 50/24 | (2012.01) |
| G08B 25/01 | (2006.01) |
| A61G 12/00 | (2006.01) |
| A61B 5/00 | (2006.01) |
| H04N 21/214 | (2011.01) |

(52) U.S. Cl.
CPC .............. *G08B 3/10* (2013.01); *G06F 19/3418* (2013.01); *G06Q 50/22* (2013.01); *G08B 5/222* (2013.01); *A61B 5/0002* (2013.01); *A61G 12/00* (2013.01); *G06F 19/322* (2013.01); *G06F 19/327* (2013.01); *G06Q 50/24* (2013.01); *G08B 25/016* (2013.01); *H04N 21/2143* (2013.01)

(58) Field of Classification Search
USPC ........................................................ 340/573.1
See application file for complete search history.

(56) References Cited

U.S. PATENT DOCUMENTS

| 5,561,412 | A  * | 10/1996 | Novak et al. ............. 340/286.07 |
| 7,526,529 | B2 * | 4/2009 | Unluturk et al. ............... 709/217 |
| 2005/0242928 | A1 * | 11/2005 | Kirkeby ................... 340/286.07 |
| 2005/0282566 | A1 * | 12/2005 | Bixler et al. ................... 455/466 |
| 2007/0004971 | A1 * | 1/2007 | Riley et al. ..................... 600/300 |
| 2008/0015900 | A1 * | 1/2008 | Denholm .......................... 705/2 |
| 2008/0018436 | A1 * | 1/2008 | Traughber et al. ........ 340/286.07 |
| 2008/0300885 | A1 * | 12/2008 | Shih et al. ...................... 704/271 |
| 2009/0212925 | A1 * | 8/2009 | Schuman et al. ......... 340/286.07 |

* cited by examiner

*Primary Examiner* — Mohamed Barakat

(74) *Attorney, Agent, or Firm* — Maxwell L. Minch; GrayRobinson, P.A.

(57) ABSTRACT

The present invention generally relates to healthcare call bells. Specifically, this invention relates to a call bell system and method for providing a need specific service identifiers and requests based on one or more criteria identified by the system.

19 Claims, 5 Drawing Sheets

SYSTEM AND METHOD FOR PROVIDING NEED SPECIFIC SERVICE IDENTIFIERS

CROSS REFERENCE TO RELATED APPLICATIONS

This application claims the benefit of U.S. Provisional Patent Application No. 61/550,911 filed Oct. 24, 2011, the entire disclosure of which is incorporated herein by reference.

FIELD OF THE INVENTION

The present invention generally relates to healthcare call bells. Specifically, this invention relates to a call bell system and method for providing need specific service identifiers and requests based on one or more criteria identified by the system.

BACKGROUND OF THE INVENTION

Efficient communication is an important and essential requirement for medical and healthcare professionals and the patients they treat. Quality communication between a patient and a healthcare professional helps ensure not only that a patient gets what they need, but also that they get what they need in an efficient manner and from the person best suited to fulfill that need. To that end, the healthcare field of today features a wide array of communications methods beyond the simple spoken and written word, including a variety of wired and wireless monitoring devices that use computers to automatically alert a healthcare professional as to the status of a patient. To this day, however, the call bell is perhaps the most recognizable and useful tool patients have for communicating with their care takers.

Currently, the call bell is typically a relatively small, handheld device that has a single button on it. The patient can depress the button on the call bell to summon assistance from a health care professional. The healthcare professional responds to the call and determines what kind of assistance the patient requires. Upon determining what assistance the patient requires, the health care professional can assist the patient or contact another healthcare professional that is more capable of assisting the patient. This system, however, is inefficient as the patient only has one signaling option no matter what the specific need of the patient is or what specific healthcare professional would be best suited to assist the patient.

Therefore there is a need in the art for a need specific call bell system that offers a patient multiple selectable buttons that each correspond to a variety of specific needs and can likewise directly alert the healthcare professional best qualified to assist the patient with a given need. These and other features and advantages of the present invention will be explained and will become obvious to one skilled in the art through the summary of the invention that follows.

SUMMARY OF THE INVENTION

Accordingly, it is an object of the present invention to provide a need specific call bell system and method which allows a user to request assistance for a specific need and to alert the responder most qualified to assist that user with that specific need.

According to an embodiment of the present invention, a need specific call bell system, the call bell system comprising of: a call bell device, including one or more need specific buttons, and a first communications means, wherein the one or more need specific buttons are communicatively connected to the first communications means, wherein the first communications means is configured to send a call request in response to a user's interaction with one or more of the one or more need specific buttons, and a remote computing device, including a call processing module, and a second communications means, wherein the call processing module is communicatively connected to the second communications means, wherein the call processing module includes physical memory instructions that cause the call processing module to, receive the call request from the call bell device, process the call request, generate a notification event based at least in part on the call request, and transmit the notification event to one or more responders.

According to an embodiment of the present invention, the call bell device is an analog device.

According to an embodiment of the present invention, the call bell device is a remote computing device.

According to an embodiment of the present invention, the one or more need specific buttons include of a separate call button for at least pain, hunger, bathroom, emergency and general assistance.

According to an embodiment of the present invention, the call processing module is configured to receive one or more call requests simultaneously.

According to an embodiment of the present invention, the physical memory storing instructions further causes the call processing module to compile a prioritized list of the one or more call requests.

According to an embodiment of the present invention, one or more responders assist the user with the call request.

According to an embodiment of the present invention, a method for providing a need specific call bell system, the method including the steps of: providing a call bell device, wherein the call bell device includes one or more need specific buttons, receiving a call request from a call bell device, wherein the call request is initiated by a user's interaction with one or more of the one or more need specific buttons, sending the call request to a call processing module of a remote computing device, processing the call request via the call processing module, generating a notification event, wherein the notification event is based at least in part on the call request, transmitting the notification event to one or more responders, wherein the notification event is displayed on a notification receiver.

According to an embodiment of the present invention, the method further includes the step of compiling a prioritized list of the one or more call requests, wherein the one or more call requests are sorted by urgency.

According to an embodiment of the present invention, the method further includes the step of assisting the user, wherein the one or more responders assist the user with the one or more call requests.

According to an embodiment of the present invention, the call request is a selection of a request type from a group of request types including pain, hunger, bathroom, emergency and general assistance.

According to an embodiment of the present invention, the method further includes the step of assigning the call request to a specific responder of the one or more responders based on one or more qualifications of the specific responder.

According to an embodiment of the present invention, the method further includes the step of assigning the call request to a specific responder of the one or more responders based on the request type.

DETAILED SPECIFICATION

The present invention generally relates to healthcare call bells. Specifically, this invention relates to a call bell system and method for providing a need specific service identifiers and requests based on one or more criteria identified by the system. In this manner, a call bell device with a plurality of buttons is connected to the system, wherein the system is configured to process the various signals sent in response to one or more button presses.

According to an embodiment of the present invention, the call bell device is configured for use in healthcare settings (e.g., hospitals, nursing homes). By providing a plurality of buttons on the call bell device, the staff can be better utilized by having the appropriate person(s) respond to specific needs of specific patients.

Figure 1:
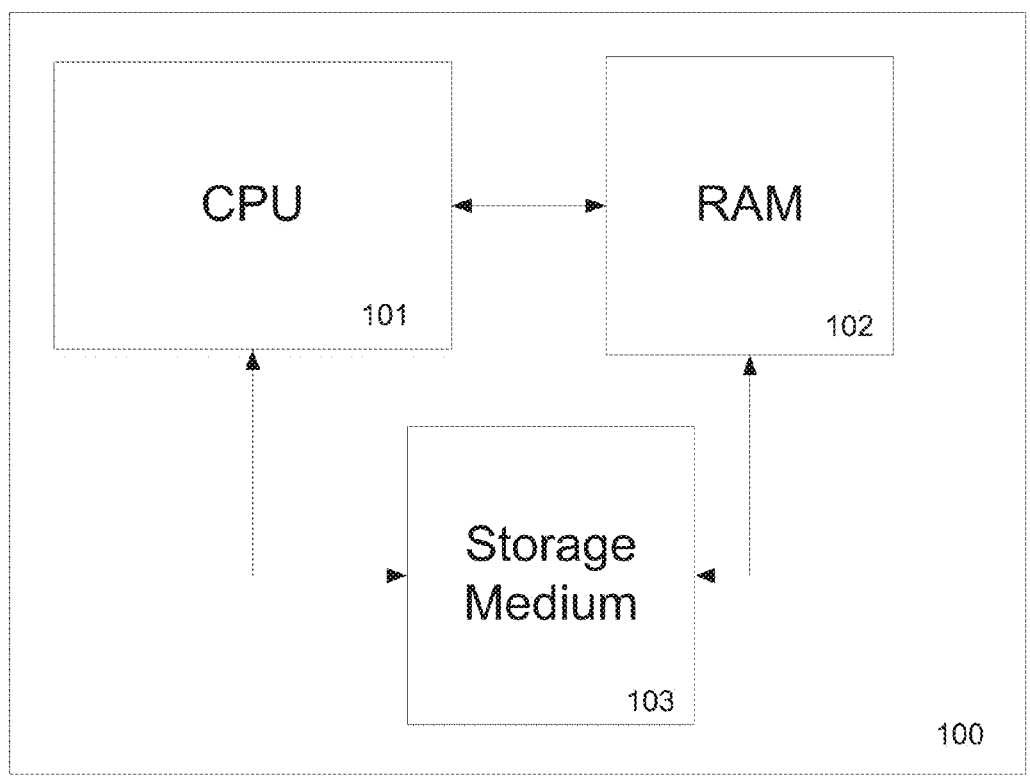
FIG. 1 shows a schematic of a computing device that may be utilized in accordance with embodiments of the present invention.

Turning now to FIG. 1 According to an embodiment of the present invention, the system and method is accomplished through the use of one or more computing devices 100. One of ordinary skill in the art would appreciate that a computing device appropriate for use with embodiments of the present application may generally be comprised of one or more of a Central processing Unit (CPU) 101, Random Access Memory (RAM) 102, and a storage medium 103 (e.g., hard disk drive, solid state drive, flash memory). Examples of computing devices usable with embodiments of the present invention include, but are not limited to, personal computers, smart phones, laptops, mobile computing devices, and servers. One of ordinary skill in the art would understand that any number of computing devices could be used, and embodiments of the present invention are contemplated for use with any computing device.

In an exemplary embodiment according to the present invention, data may be provided to the system, stored by the system and provided by the system to users of the system across local area networks (LANs) (e.g., hospital networks, home networks) or wide area networks (WANs) (e.g., the Internet, cellular transmission carriers). In accordance with the previous embodiment, the system may be comprised of numerous servers communicatively connected across one or more LANs and/or WANs. One of ordinary skill in the art would appreciate that there are numerous manners in which the system could be configured and embodiments of the present invention are contemplated for use with any configuration.

In general, the system and methods provided herein may be consumed by a user of a computing device whether connected to a network or not. According to an embodiment of the present invention, some of the applications of the present invention may not be accessible when not connected to a network, however a user may be able to compose data offline that will be consumed by the system when the user is later connected to a network.

In accordance with an embodiment of the present invention, the system is comprised of one or more application servers for electronically storing information used by the system. Applications in the servers may retrieve and manipulate information in storage devices and exchange information through a LAN.

According to an exemplary embodiment, exchange of information through the LAN or other network may occur through one or more high speed connections directed through one or more routers. Router(s) are completely optional and other embodiments in accordance with the present invention may or may not utilize one or more routers. One of ordinary skill in the art would appreciate that there are numerous ways server may connect to the LAN for the exchange of information, and embodiments of the present invention are contemplated for use with any method for connecting to networks for the purpose of exchanging information.

Users may connect to the server via the LAN or other network in numerous ways. For instance, a user may connect to the system i) through a computing device directly connected to the LAN, ii) through a computing device connected to the LAN through a routing device, iii) through a computing device connected to a wireless access point, iv) through a computing device via a wireless connection (e.g., CDMA, GMS, 3G, 4G) to the LAN or v) through a call box of the present application. One of ordinary skill in the art would appreciate that there are numerous ways that a user may connect to the server via the LAN or other network, and embodiments of the present invention are contemplated for use with any method for connecting to the server via LAN or other network.

According to an embodiment of the present invention, the need specific call bell system may include a call bell device. In a preferred embodiment, the call bell device may include one or more need specific call buttons and first communications means. In the preferred embodiment, the one or more need specific call buttons are communicatively connected to the first communications means. One of ordinary skill in the art would appreciate that the call bell device could be given similar or additional functionality with any number of optional components, and embodiments of the present invention are contemplated for use with any such component.

According to an embodiment of the present invention, the call bell device may include one or more need specific call buttons. In a preferred embodiment, the need specific call buttons may correspond to one or more of a variety of requests or needs of a user. These needs may include, but are not limited to, hunger, thirst, pain, bathroom, medicine, emergency, or general assistance. By selecting or depressing a particular need specific call button, the user would be able to request assistance for that particular need. One of ordinary skill in the art would appreciate that there are numerous concerns and requests that could be incorporated into a need specific call button, and embodiments of the present invention are contemplated for use with any such concern or request.

Figure 2:
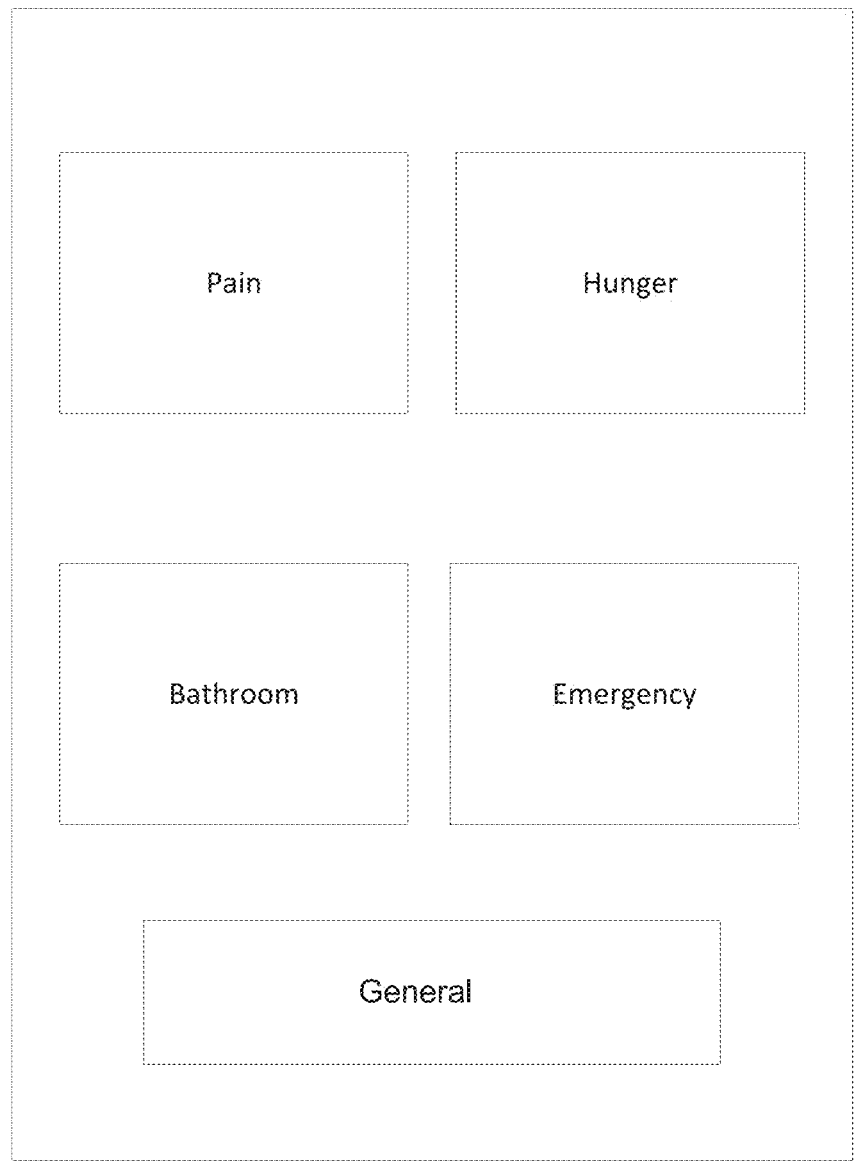
FIG. 2 shows a top view of a need specific call bell in accordance with an embodiment of the present invention.

Turning now to FIG. 2, a call box device in accordance with an exemplary embodiment of the present invention is shown. The call bell device shown in FIG. 2 has 5 buttons, representing common concerns of patients in a healthcare setting. In this exemplary embodiment, the buttons are comprised of pain, hunger, bathroom, emergency and general. Other embodiments may have a greater of fewer number of buttons, buttons with different purposes or buttons located on various regions of the call bell device. One of ordinary skill in the art would appreciate that there are numerous configurations of a call bell device that could be utilized with embodiments of the present invention, and embodiments of the present invention are contemplated for use with any plausible configuration.

According to an embodiment of the present invention, the buttons may be comprised of graphical images representing certain functions, text in numerous languages, braille or any other cognizable way of indicating to a user a particular function. Furthermore, exemplary embodiments of the present invention may have backlit buttons or otherwise illuminated buttons such that a patient or other user could find and utilize the need specific call box in the dark or low light settings. The backlit buttons may also change color to represent active requests, standby mode, hold or other indications that could be presented through the use of color specific patterns. The backlit buttons may change color in response to a status of a request as well. For instance, a button may be green when a request is open, yellow may indicate that the request has been received and is being processed and red may mean the request has been serviced and the button has returned to an inactive state. One of ordinary skill in the art would appreciate that there are numerous colors and color combinations that may be utilized with embodiments of the present invention, and embodiments of the present invention are contemplated for use with any color and color combination.

In an alternative embodiment, the call bell device may include a capacitive touch screen. The capacitive touch screen may include graphical representations of the various concerns a patient in a hospital setting may have. For example, a picture of food for hunger, a glass of water for thirst, a toilet for bathroom, a cross for an emergency, or question mark for general assistance. By touching one of the pictures of the capacitive touchscreen, a user would thereby initiate a request for the selected concern. In embodiments utilizing capacitive touch screens (or other touch sensitive displays), the graphical representations may be changed, based on any number of criteria (e.g., healthcare setting and available options, patient type, patient needs, time of day). One of ordinary skill in the art would appreciate that there are numerous graphical representations that could be depicted on the capacitive touch screen of the need specific call box, and embodiments of the present invention are contemplated for use with any such graphical representation.

In operation, the user will press a button on the call bell device when they are in need of one or more particular services. In an exemplary embodiment, the system is configured to allow for the receipt of more than one call at a time. For instance, a user may be both hungry and in pain and desire to have both of those needs handled in due course.

According to an embodiment of the present invention, the call bell device may include a first communications means. In a preferred embodiment, the first communications mean may be a wired connection including, but not limited to, CAT5, CAT6, coaxial cable, or optical wire. In an alternate preferred embodiment, the first communications means may be a wireless connection including, but not limited to, Bluetooth, infrared, Wi-Fi or any combination thereof. One of ordinary skill in the art would appreciate that the first communications means could utilize and number of mediums, and embodiments of the present invention are contemplated for use with any medium appropriate for carrying a signal.

According to an embodiment of the present invention, the need specific call bell system includes a remote computing device. In a preferred embodiment, the remote computing device may include a call processing module and a second communications means. In the preferred embodiment, the call processing module is communicatively connected to the second communications means. One of ordinary skill in the art would appreciate that the remote computing device could be given similar or additional functionality with any number of optional components, and embodiments of the present invention are contemplated for use with any such component.

According to an embodiment of the present invention, the remote computing device may include a second communications means. In a preferred embodiment, the second communications mean may be a wired connection including, but not limited to, CAT5, CAT6, coaxial cable, or optical wire. In an alternate preferred embodiment, the second communications means may be a wireless connection including, but not limited to, Bluetooth, infrared, Wi-Fi or any combination thereof. One of ordinary skill in the art would appreciate that the second communications means could utilize and number of mediums, and embodiments of the present invention are contemplated for use with any medium appropriate for carrying a signal.

According to an embodiment of the present invention, the remote computing device may include a call processing module. In a preferred embodiment, the call processing module is a central server configured to process a plurality of call requests that it receives from a plurality of call bell devices. As an illustrative example, once the user presses a button on the call bell device, a call request is sent via the first communication means of the call bell device. The call request is received by the second communications means of the remote computing device and processed by the call processing module. The call request is comprised of, at least, the identification of the type of need to be serviced and the location of the call bell device. The call request may be further comprised of other relevant information, such as date, time, information stored about the user or any combination thereof.

According to an embodiment of the present invention, the call request is processed by the call processing module where a notification event is generated. In a preferred embodiment, the notification event is made based on the information that is contained in the call request. Once the notification is generated, the call processing module is configured to transmit the notification event to the appropriate recipient to handle the request. For instance, in a hospital setting, the call processing module may be configured to send the request to the nursing station in charge of handling a particular patient who initiated the request. In other examples, the request may be sent directly to the one or more individuals in charge of handling/processing the particular request (e.g., nurse for pain, cafeteria for hunger).

According to an embodiment of the present invention, the notification event may be comprised of information pertinent to not only the type of request and location of the user, but may also comprised of information as to what type of individual is most appropriate to respond to such request. For instance, a general request may be best handled by a nurse's aide, whereas a pain request may require a nurse to attend to the request. Additional information may be utilized to help select the most appropriate individual(s) to respond to a particular request. For instance, a user who initiated a request for food who has a significant amount of food allergies or other food related complications may have their request be sent to a nutritionist or other professional designated to handle such complex requests. Other examples include bathroom requests for immobilized or overly large patients that may require the request be sent to multiple individuals or individuals of a certain size or gender (e.g., male for male bathroom request, female for female bathroom request). One of ordinary skill in the art would appreciate that there are numerous requests and appropriate responses to those requests that may be appropriate for use with embodiments of the present invention, and embodiments of the present invention are contemplated for use with any appropriate type of configuration of routing the requests.

According to an embodiment of the present invention the call processing module may be integrated with the records system at wherever it is being used. In assisting with identifying the appropriate individual to send to answer the call request, the system may have access to records of the various individuals who work in connection with the particular users requesting assistance. For instance, if a user is being treated by a specific doctor for a specific issue and a request implicates a need for that doctor to be present, that doctor could be notified by the system.

According to an embodiment of the present invention, a notification event may be displayed on a notification receiver. In a preferred embodiment, the notification receiver may be the screen(s) and computing device(s) at a nursing station, one or more mobile computing devices in the possession of the requested individual (e.g., cell phone, tablet PC, smartphone, pager). The notification event may be configured to be sent via one or more appropriate networks. For instance, notification events may be sent via one or more private LANs, one or more public LANs, one or more WANs or any combination thereof. Notification events may also be provided to one or more mobile computing devices by way of wireless connections, such as Bluetooth, CDMA, GSM or Wi-Fi connections, thereby allowing individuals to receive notifications no matter where they are.

According to an embodiment of the present invention, a notification event may include a notification message containing information pertinent to the specific call request. For instance, notification messages may include, but are not limited to, name of the user, type of request, time of the request, any special needs, information regarding a request for multiple individuals to service the request, warnings, priority and time to service the request. One of ordinary skill in the art would appreciate that there are numerous types of information that could be utilized with notification messages of the present invention, and embodiments of the present invention are contemplated for use with any type of information.

According to an embodiment of present invention, notifications may also be configured to cause an alert to occur on the individual's computing device. For instance, an audible tone may be played or the notification may cause a force feedback device to activate (e.g., vibrate).

According to an embodiment of the present invention, the system may be configured to compile a prioritized list of all call requests that are received. In a preferred embodiment, the list would be organized by importance, with critical and urgent call requests being handled before routine and minor call requests. As an illustrative example, a pain request may be prioritized to be handled prior to a general request. Furthermore, requests may be configured to weigh the amount of time that has elapsed since the requests was initiated, so that prioritization also takes into account the length of time a user has been waiting to receive assistance.

According to an embodiment of the present invention, a notification event may be removed from the system or marked as complete after the call request has been answered. In a preferred embodiment, an additional notation of pertinent information may be included in a report that contains details about how the call request was resolved or what additional actions are required. As an illustrative example, after a pain request has been serviced, the notification may be released and the dosage and type of pain medication given to the user may be recorded in the system. In this manner, repeated requests may be identified, especially in the case where repeating the service may cause injury or harm to the user.

According to an embodiment of the present invention, the request may be marked as complete in one or more manners. In one preferred embodiment, the button on the need specific call bell may be pressed again, turning the request into an off-state or ready-state. In other embodiments, the individual servicing the request can mark the request complete on their computing device. In this manner, any additional pertinent information may also be recorded at this time. In still further embodiments, computing devices in the user's room or area can be utilized to complete a request and enter relevant information. Additionally, a request may be marked complete and a computing device may be utilized to update or add information pertaining to the request at a later time.

According to an alternate embodiment of the present invention, sensors and/or networks may be utilized to automatically identify when an individual servicing a request has entered and exited the user's area. For instance, the user's area (e.g., hospital room) may be identified by a short range network (e.g., Near-Field network, Bluetooth network). When an individual enters the user's area, the short range network identifies the individual's computing device and may mark the request as "in-process" or another status indicating the individual has entered the user's area. Once the individual is done, and leaves the user's area, the request may be automatically marked as complete. In alternate embodiments, when an individual leaves the user's area, the individual's computing device may provide a notification to the individual querying if the request should be marked complete or some other status (e.g., additional service needed). In further embodiments, various levels of request statuses may be utilized. For instance, request status could be one or more of "in-progress," "on hold," "reserved," or "high-priority." One of ordinary skill in the art would appreciate that there are numerous statuses that may be utilized with embodiments of the present invention, and embodiments of the present invention are contemplated for use with any status type.

According to an alternate embodiment of the present invention, if an individual enters a user's area with an active request, where that individual is not the assignee of the active request, the system may be configured to take one or more actions. First, the system may alert the individual of the pending request and allow that individual to service the request, assuming the individual is of an appropriate type (e.g., if a nurse enters an area with a nurse appropriate request, the nurse may service that request). The system may also provide all pertinent information about the user and the request to the computing device of that individual. Where the individual is not of an appropriate type, the system may be configured to either not alert the individual or alert the individual that there is a request, but inform the individual not to handle the request (e.g., notify the individual to tell the user that the appropriate individual will be available shortly). Additionally, if an appropriate individual decides not to service the request after being notified, the request will remain active for the originally intended individual to service.

According to an embodiment of the present invention, the system may be configured to allow servicing individuals to pass or trade requests among themselves. In this manner, even though the system may deem a particular individual appropriate to service a task, due to extenuating circumstances, that individual may not desire to or be capable of servicing a particular request. In this manner, the system may be configured to allow for manual load balancing and request distribution.

In an alternate embodiment, the need specific call bell may also be comprised of additional controls for other functionality. For instance, additional controls may include, but are not limited to, TV controls, light controls, phone controls, bed adjustment controls or any combination thereof. One of ordinary skill in the art would appreciate that there are numerous types of controls that could be utilized with embodiments of the present invention, and embodiments of the present invention are contemplated for use with any appropriate type of controls.

Exemplary Embodiments

Figure 3:
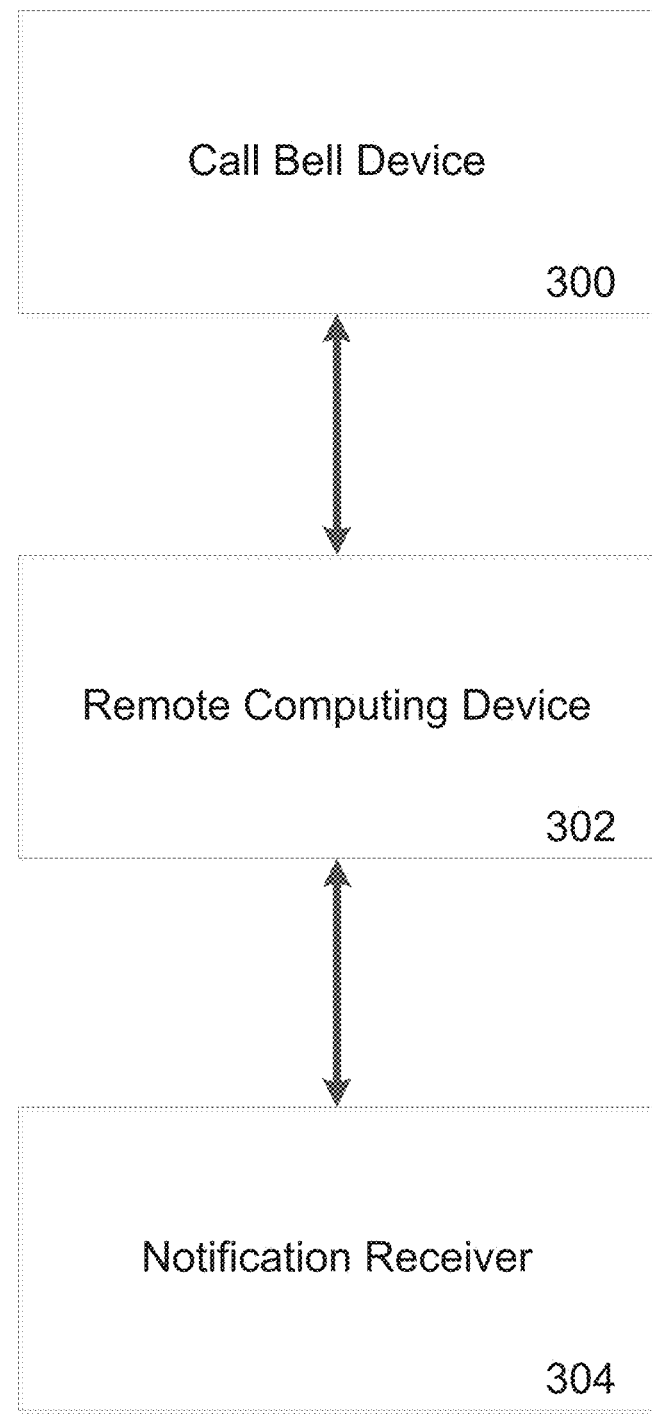
FIG. 3 is a schematic overview of a need specific call bell system, in accordance with a preferred embodiment on the present invention.

Turning now to FIG. 3, a schematic overview of a preferred embodiment of a need specific call bell system is shown. In this embodiment, the need specific call bell system includes a call bell device 300, a remote computing device 302, and a notification receiver 304. In this embodiment, the call bell device 302 sends a call request to the remote computing device 302. The remote computing device 302, then processes the call request into a notification event, which is send to the notification receiver 304. While the embodiment shown in FIG. 3 is an exemplary embodiment, other embodiments may include additional or fewer components. One of ordinary skill in the art would appreciate that there are numerous configurations of the components that could be utilized with embodiments of the present invention, and embodiments of the present invention are contemplated for use with any configuration of components.

Figure 4:
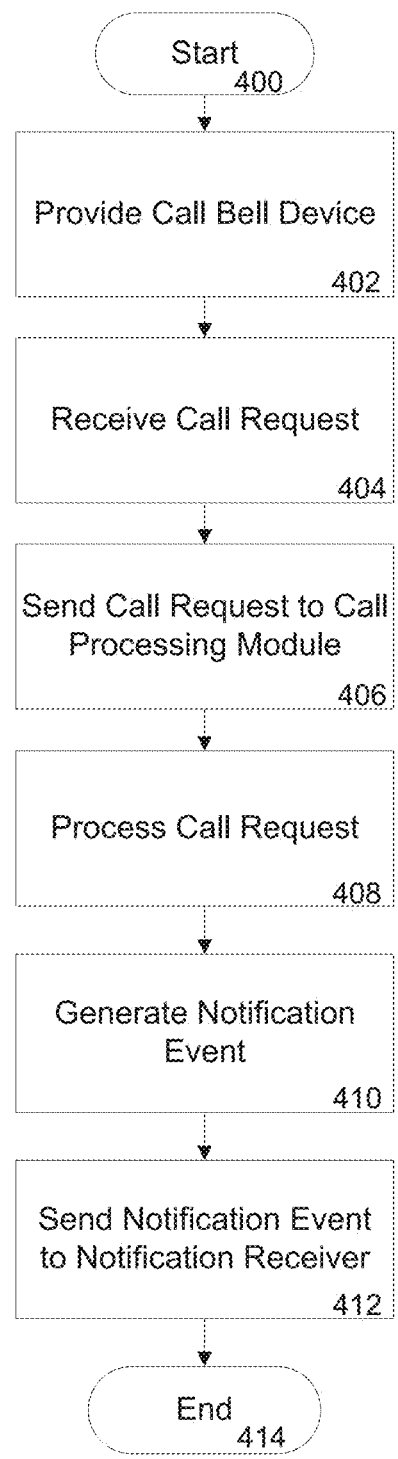
FIG. 4 is a process flow of an exemplary method for a need specific call bell, in accordance with an embodiment of the present invention.

The following is an exemplary embodiment of a method for utilization of the need specific call bell as shown in FIG. 4. At step 400, the process starts with a user requiring assistance.

At step 402, a call bell device is provided to the user. The user is able to use the call bell device to request assistance.

At step 404, a call request is received. The call request is initiated by the user interacting with one or more need specific buttons that are present on the call bell device.

At step 406, the call request is sent to a call processing module. The call processing module is a component of a remote computing device that is capable of managing one or more call requests.

At step 408, the call request is processed by the call processing module. The call processing module is capable of prioritizing the one or more call requests that it receives.

At step 410, a notification event is generated. The call request module generates a notification event based on the information it receives as a part of the call request.

At step 412, the notification event is sent to a notification receiver. The notification receiver is one of any number of devices capable of displaying the information of a call request to one or more responders.

At step 414, the process ends, with one or more responders receiving the notification event and responding to that notification event as necessary.

Figure 5:
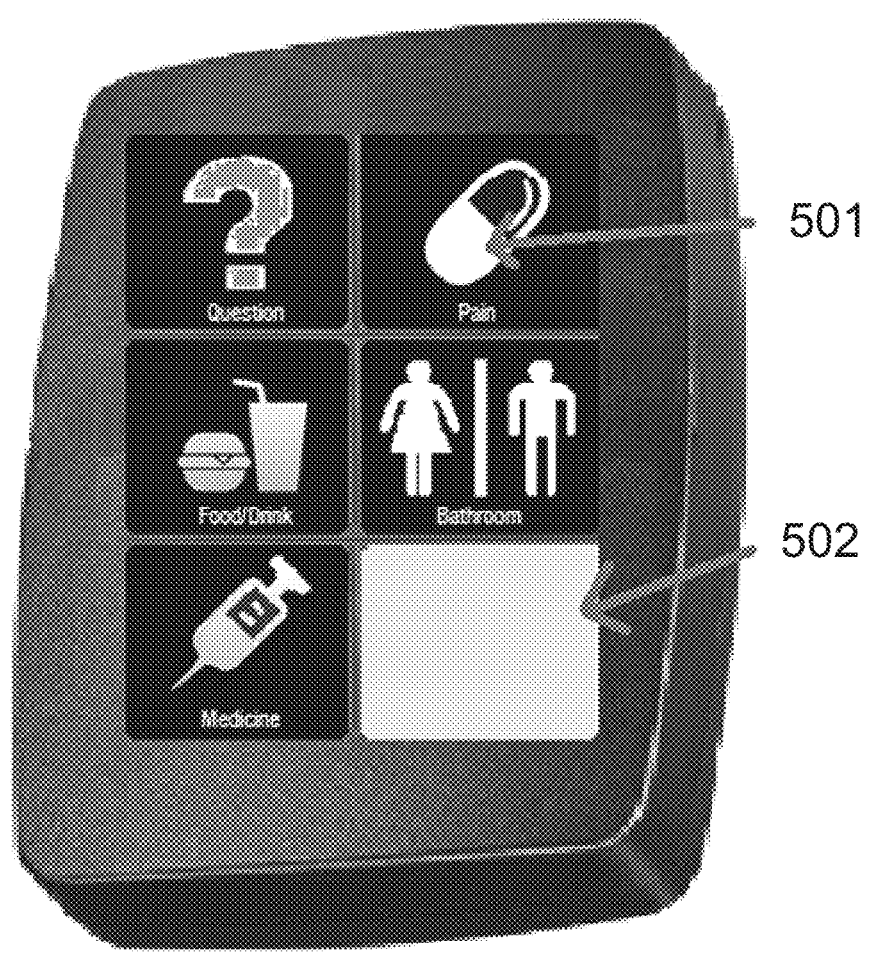
FIG. 5 is a perspective view of an exemplary embodiment of a need specific call bell, in accordance with an embodiment of the present invention.

Turning now to FIG. 5, an exemplary embodiment of the present invention is shown. In this embodiment, the need specific call bell device has numerous need specific buttons (e.g., 501). The need specific call bell device shown in FIG. 5 also has interchangeable need specific buttons, allowing for the labels and purpose for each call bell button to be changed based on various criteria. For instance, need specific call bell button labels may be changed based on the patient's needs (e.g., braille for blind patients, multi-lingual need specific buttons, remove non-relevant buttons). In this manner, embodiments of the present invention may be customized ad hoc for each individual patient or setting. This allows greater flexibility for the system and the users thereof. In certain embodiments, the need specific call bell device may detect which need specific label is placed on each button of the need specific call bell device (e.g., via RFID, via barcode, via QR code) allowing the system to automatically recognize the needs to be handled by the device and route requests accordingly.

While embodiments of the invention discussed in this disclosure have largely focused on the use of the invention in a hospital or similar health care setting, one of skill in the art would appreciate that the invention may be adapted to work in a variety of settings. As an example, another important setting for which the invention could be adapted is for use in an assisted living or nursing home. The invention may also be adapted to be used in an educational setting, as a customer service application, or as a labor and resources management application.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

The invention claimed is:

1. A need specific call bell system, said call bell system comprising:

a call bell device, comprising
   a processor;
   a first communication means; and
   a plurality of need specific buttons,
   wherein selecting a need specific button of the plurality of need specific buttons initiates a need specific call request corresponding to the need specific button, wherein each button of the plurality of need specific buttons corresponds to a different need and/or condition including: pain, hunger, bathroom, emergency, and general assistance, wherein said need specific call request identifies a location of the call bell device, wherein one or more need specific call request is transmitted from said call bell device, via said first communication means, when one or more of said buttons corresponding to said respective needs and/or conditions is selected by a requester, wherein two or more need specific call requests are transmitted simultaneously from said call bell device, via said first communication means, when two or more of said buttons corresponding to said respective needs and/or conditions are selected by the requester;

a remote computing device comprising
   a second communication means; and
   a call processing module;
   wherein said call processing module is configured to receive, via said second communication means, one or more need specific call requests from said call bell device;
   wherein said call processing module assigns each of said one or more need specific call requests to a specific responder of one or more responders based on one or more qualifications of the specific responder with respect to the need and/or condition of each of said one or more need specific call requests, wherein the one or more qualifications are based on the job responsibilities of the responder or the responders department;
   wherein said call processing module is further configured to process said one or more need specific call requests, generate a notification event based on each need specific call request, and transmit, via said second communication means, said notification event to an assigned responder;

wherein said call processing module transmits each notification event to a corresponding assigned responder, wherein said each notification event is displayed on a notification receiver, wherein an assigned responder who receives the need specific call request is prompted to selectively either respond to the request or transfer the request to another responder.

2. The need specific call bell system of claim 1, wherein said call bell device is an analog device.

3. The need specific call bell system of claim 1, wherein said call bell device is a remote computing device.

4. The need specific call bell system of claim 1, wherein said call processing module is configured to receive one or more need specific call requests simultaneously.

5. The need specific call bell system of claim 1, wherein said call processing module is configured to compile a prioritized list of said one or more need specific call requests, wherein said one or more need specific call requests are prioritized based on one or more of the following: (1) urgency of the need specific call request, (2) seriousness of the need specific call request, and (3) length of time a requester has been waiting to receive assistance.

6. The need specific call bell system of claim 1, wherein the notification event further comprises information identifying the type of responder that is most appropriate to respond to the need specific call request.

7. The need specific call bell system of claim 6, wherein the most appropriate type of responder is a nutritionist.

8. The need specific call bell system of claim 6, wherein when the need specific call request is a request for bathroom assistance the most appropriate responder is determined based at least in part on the gender of the requester and responder.

9. The need specific call bell system of claim 6, wherein the most appropriate type of responder is determined based at least in part on medical records.

10. The need specific call bell system of claim 1, further comprising a sensor configured to detect when the assigned responder enters or exits a requester's area.

11. The need specific call bell system of claim 10, wherein a need specific call request status is marked as "in progress" when said sensor detects that the assigned responder has entered the requester's area.

12. The need specific call bell system of claim 10, wherein a need specific call request status is marked as complete when the assigned responder is done and said sensor detects that the assigned responder has exited the requester's area.

13. The need specific call bell system of claim 1, wherein a need specific call request status is selected from the group consisting of: active, in-progress, on hold, reserved, high-priority, or complete.

14. The need specific call bell system of claim 1, wherein a need specific call request status remains active until the assigned responder services the request.

15. The need specific call bell system of claim 1, wherein the call bell device includes a capacitive touch screen, wherein the need specific buttons are selectable computer generated graphical representations depicted on said touch screen, wherein said buttons may be programmatically added, deleted, or substituted as needed.

16. A method for providing a need specific call bell system, said method comprising the steps of:

providing a call bell device, wherein said call bell device comprises a plurality of need specific buttons, wherein each need specific button of the plurality of need specific buttons corresponds to a different need and/or condition including: pain, hunger, bathroom, emergency, and general assistance;

selecting one or more need specific button to initiate corresponding one or more need specific call request corresponding to the one or more need specific button, wherein said one or more need specific call request identifies a location of the call bell device;

transmitting one or more need specific call request from said call bell device when one or more of said buttons corresponding to said respective needs and/or conditions is selected by a requester;

transmitting two or more need specific call requests simultaneously from said call bell device when two or more of said buttons corresponding to said respective needs and/or conditions are selected by the requester;

receiving the one or more need specific call requests at a call processing module of a remote computing device;

processing the one or more need specific call requests via said call processing module;

assigning each of said one or more need specific call requests to a specific responder of one or more responders based on one or more qualifications of the specific responder with respect to the need and/or condition of each of said one or more need specific call requests, wherein the one or more qualifications are based on the job responsibilities of the responder or the responders department;

generating a notification event, wherein said notification event is based at least in part on one or more of said need specific call requests; and transmitting said notification event to a corresponding assigned responder, wherein said notification event is displayed on a notification receiver, wherein an assigned responder who receives the need specific call request is prompted to selectively either respond to the request or transfer the request to another responder.

17. The method of claim 16, further comprising the step of compiling a prioritized list of said one or more need specific call requests, wherein said one or more need specific call requests are prioritized based on one or more of the following: (1) urgency of the need specific call request, (2) seriousness of the need specific call request, and (3) length of time a requester has been waiting to receive assistance.

18. The method of claim 16, wherein the notification event is marked as complete after the need specific call request has been answered.

19. The method of claim 18, wherein a report is generated that contains details about how the need specific call request was resolved and what additional actions may be required.

* * * * *